United States Patent [19]

Murdock et al.

[11] Patent Number: 4,888,137

[45] Date of Patent: Dec. 19, 1989

[54] NOVEL 1,4-BIS(SUBSTITUTED-AMINO)-5,8-DIHYDROXYANTHRAQUINONES AND LEUCO BASES THEREOF

[75] Inventors: Keith C. Murdock, Pearl River, N.Y.; Frederick E. Durr, Ridgewood, N.J.

[73] Assignee: American Cyanamid Company, Wayne, N.J.

[21] Appl. No.: 42,779

[22] Filed: Apr. 27, 1987

Related U.S. Application Data

[60] Continuation-in-part of Ser. No. 485,143, Apr. 15, 1983, abandoned, which is a division of Ser. No. 244,452, Nov. 2, 1981, Pat. No. 4,430,501, which is a division of Ser. No. 63,285, Aug. 2, 1979, Pat. No. 4,278,689, which is a division of Ser. No. 923,602, Jul. 11, 1978, Pat. No. 4,197,249, which is a continuation-in-part of Ser. No. 873,040, Jan. 30, 1978, abandoned, which is a continuation-in-part of Ser. No. 824,872, Aug. 15, 1977, abandoned.

[51] Int. Cl.$^4$ ............................................. C07C 103/75
[52] U.S. Cl. ............................................................ 552/248
[58] Field of Search ................. 260/377; 514/616, 680

[56] References Cited

U.S. PATENT DOCUMENTS 3,446,817  5/1969  Harvey et al. ...................... 260/377

FOREIGN PATENT DOCUMENTS 2116555  10/1972  Fed. Rep. of Germany ...... 260/377

Primary Examiner—Richard L. Raymond
Assistant Examiner—Raymond Covington
Attorney, Agent, or Firm—Kenneth J. Dow; Edward A. Conroy, Jr.

[57] ABSTRACT

This disclosure describes symmetrical 1,4-bis(substituted-amino)-5,8-dihydroxyanthraquinones useful as chelating agents and for inducing regression and/or palliation of cancer diseases in mammals.

10 Claims, No Drawings

NOVEL 1,4-BIS(SUBSTITUTED-AMINO(-5,8-DIHYDROX-YANTHRAQUINONES AND LEUCO BASES THEREOF

CROSS REFERENCE TO RELATED APPLICATION

This application is a continuation-in-part of our copending application Ser. No. 485,143, filed Apr. 15, 1983, now abandoned which is a division of application Ser. No. 244,452, filed Nov. 2, 1981, now U.S. Pat. No. 4,230,501 which is a division of application Ser. No. 63,285, filed Aug. 2, 1979, now U.S. Pat. No. 4,278,689 which is a division of application Ser. No. 923,602, filed July 11, 1978, now U.S. Pat. No. 4,197,249 which is a continuation-in-part of abandoned application Ser. No. 873,040, filed Jan. 30, 1978 which is a continuation-in-part of abandoned application Ser. No. 824,872, filed Aug. 15, 1977.

BRIEF SUMMARY OF THE INVENTION

This invention relates to new organic compounds and, more particularly, is concerned with novel symmetrical derivatives of 1,4-bis(2-amino-ethylamino)-5,8-dihydroxyanthraquinone having the following structural formula:

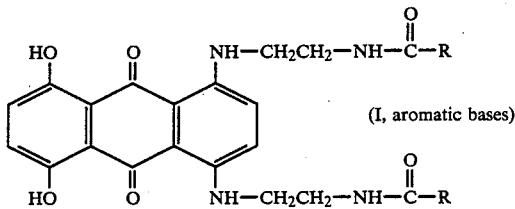

(I, aromatic bases)

wherein R is hydrogen, alkyl having from one to three carbon atoms, trifluoromethyl, acetyl, ethoxy or carbomethoxy. Also included within the purview of the present invention are the leuco bases and tautomers thereof which may be represented by the following general formulae:

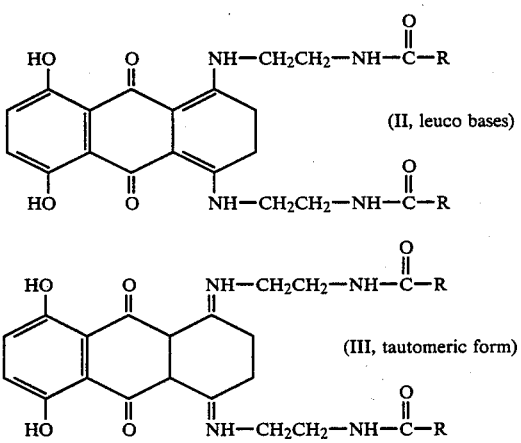

(II, leuco bases)

(III, tautomeric form)

wherein R is as hereinabove defined.

DETAILED DESCRIPTION OF THE INVENTION

The novel compounds of the present invention are obtainable as reddish brown to blue black crystalline materials having characteristic melting points and absorption spectra and which may be purified by leaching with lower alkanol since many of the free bases are insoluble in water and some of them are insoluble in most organic solvents. The organic bases of this invention (I, II and III) form non-toxic acid addition salts with a variety of pharmacologically acceptable organic and inorganic salt-forming reagents. Thus, acid-addition salts, formed by admixture of the organic free base with 1,2 or up to eight equivalents of an acid, suitably in a neutral solvent are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, toluene, and the like.

The novel compounds of the present invention may be readily prepared by treating 1,4-bis(2-amino-ethylamino)-5,8- dihydroxyanthraquinone with a variety of reagents such as:
(a) acetic-formic anhydride in 90% formic acid;
(b) acetic anhydride, propionic anhydride, iso-butyric anhydride or n-butyric anhydride in an inert solvent such as dioxane or chloroform;
(c) trifluoroacetic anhydride in glacial acetic acid;
(d) ethyl pyruvate in N,N-dimethylformamide;
(e) ethyl chloroformate in pyridine; and
(f) dimethyl oxalate in N,N-dimethylformamide; all at ambient temperatures for a period of from a few hours to a few days. The leuco bases (II) may be readily oxidized to the fully aromatic derivatives (I) by a variety of methods such as air oxidation or treatment with hot nitrobenzene, or treatment with chloranil, hydrogen peroxide, or sodium perborate.

The novel compounds described herein are useful as chelating, complexing or sequestering agents. The complexes formed with polyvalent metal ions are particularly stable and usually soluble in various organic solvents. These properties, of course, render them useful for a variety of purposes wherein metal ion contamination presents a problem; e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds. In addition, the leuco bases (II) are useful as intermediates in the preparation of the fully aromatic derivatives (I).

The novel compounds of the present invention also possess the property of inducing regression and/or palliation of cancer diseases in mammals as established by the following tests.

Lymphocytic leukemia P388 test

The animals used are DBA/2 mice all of one sex, weighing a minimum of 17 g. and all within a 3 gram weight range. There are 5 or 6 animals per test group. The tumor transplant is by intraperitoneal injection of 0.1 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60-mg./kg. injection or 1,4-dihydroxy-5,8-bis[2-(2-hydroxyethylamino)ethylamino]anthraquinone dihydrochloride (U.S. Pat. No. 4,197,249) given at the indicated doses by injection. The results of this test with representative compounds of the present invention appear in Table I. The criterion for efficacy is T/C×100⩾125%.

Melanotic Melanoma B16

The animals used were C57BC/6 mice, all of the same sex, weighing a minimum of 17 g and all with a 3 g weight range. There are normally 10 animals per test group. A 1.0 g portion of melanotic melanoma B16 tumor was homogenized in 10 ml of cold balanced salt solution and a 0.5 ml aliquot of the homogenate was implanted intraperitoneally into each of the test mice. The test compounds were administered intraperitoneally on days one through nine (relative to tumor inoculation) at various doses. The animals were weighed and survivors recorded on a regular basis for 60 days. The median survival time and the ratio of survival time for treated (T)/control (C) animals were calculated. The positive control compound was 1,4-dihydroxy-5,8-bis-[[2-(2-hydroxyethylamino)ethyl]amino]anthraquinone, dihydrochloride (U.S. Pat. No. 4,197,249) given at the indicated doses by injection. The results of this test with representative compounds of the present invention appear in Table II.

Also embraced within the purview of the present invention are therapeutic compositions of matter containing the novel derivatives of the present invention. This aspect of the invention includes the novel compositions of matter and the method of inducing the regression and/or palliation of leukemia and related cancers in mammals when administered in amounts ranging from about one mg to about 1.2 g. per square meter of body surface area per day. The interrelationship of dosages for animals of various sizes and species and humans (based on mg/m² of surface area) is described by Freireich, E. J., et al., Quantitative Comparison of Toxicity of Anticancer Agents in Mouse, Rat, Hamster, Dog, Monkey and Man. Cancer Chemother. Rep. 50, No. 4, 219–244, May 1966. A preferred dosage regimen for optimum results would be from about 3 mg/m²/day to about 200 mg/m²/day, and such dosage units are employed that a total of from about 5 mg to about 360 mg of the active compound for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular, or subcutaneous routes.

TABLE I

| Compound | Dose (mg/kg) | Median Survival (Days) | T/C × 100 (%) |
|---|---|---|---|
| 2,2'-[(9,10-Dihydro-5,8-dihydroxy-9,10-dioxo-1,4-anthracenediyl)bis(imino-2,1-ethanediylimino)]bis-[2-oxoacetic acid]dimethyl ester | 200 | 23 | 209 |
|  | 50 | 20.5 | 186 |
|  | 12 | 19.5 | 177 |
|  | 3 | 16 | 145 |
| Control | — | 11 | — |
| 1,4-dihydroxy-5,8-bis[2-(2--hydroxyethylamino)ethyl--amino]anthraquinone dihydrochloride | 1.6 | >30 | >273 |
|  | 0.4 | >30 | >273 |
|  | 0.1 | 14.5 | 132 |
| [(9,10-Dihydro-5,8-dihydroxy-9,10-dioxo-1,4-anthracenediyl)bis(imino-2,1-ethanediyl)]bis[carbamic acid]diethyl ester | 50 | 21.5 | 215 |
|  | 12 | 21 | 210 |
|  | 3 | 17 | 170 |
|  | 0.8 | 14 | 140 |
|  | 0.2 | 11 | 110 |
| Control | — | 10 | — |
| 1,4-dihydroxy-5,8-bis[2-(2--hydroxyethylamino)ethyl--amino]anthraquinone dihydrochloride | 1.6 | >30 | >300 |
|  | 0.4 | 27 | 270 |
|  | 0.1 | 25.5 | 255 |
|  | 0.025 | 17 | 170 |
| N,N'—[(9,10-Dihydro-5,8-dihydroxy-9,10-dioxo-1,4-anthracenediyl)bis(imino-2,1-ethanediyl)]bis[2-oxo-propanamide] | 200 | 16.5 | 150 |
|  | 50 | 13.5 | 123 |
| Control | — | 11 | — |
| 1,4-dihydroxy-5,8-bis[2-(2--hydroxyethylamino)ethyl--amino]anthraquinone dihydrochloride | 1.6 | >30 | >273 |
|  | 0.4 | 19 | 173 |
|  | 0.1 | 16.5 | 150 |
| N,N'—[5,8-Dihydroxy-1,4-anthraquinonylenebis(imino-ethylene)][N—2-hydroxyethyl-acetamide-2,2'-diacetate] | 200 | 17 | 179 |
|  | 50 | 16 | 168 |
|  | 12 | 14 | 147 |
|  | 3 | 10 | 105 |
|  | 0.8 | 11 | 116 |
| Control | — | 9.5 | — |
| 1,4-dihydroxy-5,8-bis[2-(2--hydroxyethylamino)ethyl--amino]anthraquinone dihydrochloride | 3.2 | >30 | >316 |
|  | 1.6 | >30 | >316 |
|  | 0.8 | 18 | 189 |
|  | 0.4 | 19.5 | 205 |
|  | 0.2 | 14.5 | 153 |
| N,N'—(5,8-Dihydroxy-1,4-anthraquinonylene)bis[2,2,2-trifluoro-N—[2-(2,2,2-tri-fluoro-N—2-hydroxyethylacet-amido)ethyl]acetamide]-tetrakis(trifluoroacetate) (tetraester) | 6.4 | 26.5 | 230 |
|  | 1.6 | 19.5 | 170 |
|  | 0.4 | 15 | 130 |
|  | 0.1 | 16 | 139 |
|  | 0.025 | 13.5 | 117 |
| Control | — | 11.5 | — |
| 1,4-dihydroxy-5,8-bis[2-(2--hydroxyethylamino)ethyl--amino]anthraquinone dihydrochloride | 3.2 | >30 | >261 |
|  | 1.6 | >30 | >261 |
|  | 0.8 | 18 | 156 |
|  | 0.4 | 19.5 | 169 |
|  | 0.2 | 14.5 | 126 |

TABLE II

| Compound | Dose (mg/kg) | Median Survival (Days) | T/C × 100 (%) |
|---|---|---|---|
| 2,2'-[(9,10-Dihydro-5,8-dihydroxy-9,10-dioxo-1,4-anthracenediyl)bis(imino-2,1-ethanediylimino)]bis-[2-oxoacetic acid]dimethyl ester | 50 | >60 | >293 |
|  | 12 | 31.5 | 154 |
|  | 3 | 26.5 | 129 |
|  | 0.8 | 23.5 | 155 |
| Control | — | 20.5 | — |
| 1,4-dihydroxy-5,8-bis[2-(2--hydroxyethylamino)ethyl--amino]anthraquinone dihydrochloride | 1.6 | >60 | >293 |
|  | 0.4 | >60 | >293 |
|  | 0.1 | 39 | 190 |
|  | 0.025 | 33 | 161 |
| [(9,10-Dihydro-5,8-dihydroxy-9,10-dioxo-1,4-anthracenediyl)bis(imino-2,1-ethanediyl)]bis[carbamic acid]diethyl ester | 100 | 38.5 | 204 |
|  | 25 | >60 | >317 |
|  | 6 | 39.5 | 209 |
|  | 1.5 | 29.5 | 156 |
| Control | — | 18.9 | — |

TABLE II-continued

| Compound | Dose (mg/kg) | Median Survival (Days) | T/C × 100 (%) |
|---|---|---|---|
| 1,4-dihydroxy-5,8-bis[2-(2-hydroxyethylamino)ethyl-amino]anthraquinone dihydrochloride | 1.6 | 38 | 200 |
|  | 0.4 | >60 | >317 |
|  | 0.1 | 31.5 | 166 |
|  | 0.025 | 26 | 137 |
| N,N'—(9,10-Dihydro-5,8-dihydroxy-9,10-dioxo-1,4-anthracenediyl)bis(imino-2,1-ethanediyl)]bis[2-oxo-propanamide] | 100 | 38 | 158 |
|  | 50 | 41 | 171 |
|  | 25 | 43.5 | 182 |
| Control | — | 24.0 | — |
| 1,4-dihydroxy-5,8-bis[2-(2-hydroxyethylamino)ethyl-amino]anthraquinone dihydrochloride | 1.6 | >60 | >250 |
|  | 0.4 | >60 | >250 |
|  | 0.1 | 32 | 133 |
| N,N'—[5,8-Dihydroxy-1,4-anthraquinonylenebis(imino-ethylene)]bis[N—2-hydroxy-ethylacetamide-2,2'-diacetate] | 50 | 21.5 | 106 |
|  | 12 | 20.5 | 101 |
|  | 3 | 21.5 | 106 |
|  | 0.8 | 21.5 | 106 |
| Control | — | 20.2 | — |
| 1,4-dihydroxy-5,8-bis[2-(2-hydroxyethylamino)ethyl-amino]anthraquinone dihydrochloride | 1.6 | >60 | >297 |
|  | 0.8 | 35 | 173 |
|  | 0.4 | 36 | 178 |
|  | 0.2 | 32 | 158 |
| N,N'—(5,8-Dihydroxy-1,4-anthraquinonylene)bis[2,2,2-trifluoro-N—[2-(2,2,2-trifluoro-N—2-hydroxyethylacet-amido)ethyl]acetamide]-tetrakis(trifluoroacetate) (tetraester) | 12 | 42 | 205 |
|  | 3 | >52 | >254 |
|  | 0.8 | 34 | 166 |
|  | 0.2 | 27 | 132 |
|  | 0.05 | 27 | 132 |
| Control | — | 20.5 | — |
| 1,4-dihydroxy-5,8-bis[2-(2-1-hydroxyethylamino)ethyl-amino]anthraquinone dihydrochloride | 1.6 | >60 | >293 |
|  | 0.4 | >60 | >293 |
|  | 0.1 | 36 | 176 |
|  | 0.025 | 28 | 137 |

The active compounds may be administered parenterally or intraperitoneally. Solutions or dispersions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars of sodium chloride. Prolonged absorption of the injectable compositions can be brought about by the use in the compositions of agents delaying absorption, for example aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium an the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for each of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered, Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

Leuco-1,4-bis(2-aminoethylamino)-5,8-dihydroxyanthraquinone

A reaction mixture comprising 10.97-g. of leuco-1,4,5,8-tetrahydroxyanthraquinone in 80 ml. of de-aerated N,N,N',N'-tetramethylethylenediamine containing 7.22 g. of ethylenediamine is heated and stirred under nitrogen at 48°–50° C. for one hour. The mixture is allowed to stand under a slow flow of nitrogen, producing a solid which is collected and washed with ethyl acetate, acetonitrile and petroleum ether giving 13.8 g. of the desired product as a red-black solid.

EXAMPLE 2

Leuco-1.4-bis[2-(2-hydroxyethylamino)ethylamino]-5,8-dihydroxyanthraquinone

A suspension of 12.5 g. of 2-(2-amino-ethylamino)ethanol in 40 ml. of N,N,N',N'-tetra-methylethylenediamine is stirred and de-aerated by bubbling nitrogen in for 15 minutes. A 10.97-g. portion of leuco-1,4,5,8-tetrahydroxyanthraquinone is gradually added with stirring. The suspension is heated and stirred under nitrogen in an oil bath at 50°–52° C. for 5 hours. The mixture is allowed to stand and cool under nitrogen for 12 hours. The solid is collected by decantation, macerated in ethanol, collected and washed with ethanol giving 15.06 g. of the desired product as a green-gray solid, m.p. 129°–131° C.

EXAMPLE 3

Leuco-1,4-bis[2-[di($\beta$-hydroxyethyl)amino]ethylamino]-8-dihydroxyanthraquinone A solution of 17.8 g. of N,N-di(2-hydroxyethyl)ethylenediamine in 100 ml. of methanol is cooled with an ice bath, stirred, and de-aerated by bubbling in nitrogen for 15 minutes. A 10.97-gram portion of leuco-1,4,5,8-tetrahydroxyanthraquinone is gradually added with stirring and continued cooling. The suspension is heated and stirred under nitrogen in an oil bath at 50°–52° C. for one hour and the mixture is then allowed to stand and cool under nitrogen overnight. The solid is collected and washed with ethanol giving 14.8 g. of a red-brown solid, m.p. 165°–168° C.

EXAMPLE 4

1,4-Bis[2-(methylamino)ethylamino]-5,8-dihydroxyanthraquinone dihydrochloride

To a suspension of 11.60 g. (0.03 mole) of leuco-1,4-bis[2-(methylamino)ethylamino]-5,8-dihydroxyanthraquinone in 200 ml. of 2-methoxyethanol was added gradually with stirring 15 ml. of 8N ethanolic hydrogen chloride. The system was chilled with an ice bath and stirred as 7.50 g. (0.0305 mole) of chloranil powder was gradually added. The mixture was stirred overnight at room temperature and diluted with 600 ml. of ether. The solid was collected and washed with tetrahydrofuran. The product (14.16 g.) was recrystallized by dissolving it in 130 ml. of water and adding 650 ml. of acetone to give 13.15 g. of a blue-black solid.

EXAMPLE 5

1,4-Bis(2-aminoethylamino)-5,8-dihydroxyanthraquinone dihydrochloride

Oxidation with chloranil of 28.25 g. of the product of Example 1 by the procedure of Example 4 gives 29.66 g. of a crude, blue-black solid which is then extracted by stirring for 14 hours with 800 ml. of water. Solids are removed by centrifugation and the supernatent solution freeze-dried, leaving 16.38 g. of a blue-black solid which is unmelted by 350° C.

EXAMPLE 6

1,4-Bis[2-(2-hydroxyethylamino)ethylamino]-5,8-dihydroxyanthraquinone Dihydrochloride Chloranil oxidation of 17.86 g. of the product of Example 2 by the procedure of Example 4 gives (without recrystallization) 21.34 g. of blue-black solid, m.p. 203°–205° C.

EXAMPLE 7

1,4-Bis[2-(2-hydroxyethylamino)ethylamino]-5,8-dihydroxyanthraquinone

In a modification of the synthesis of Example 2 the solvent used is 100 ml. of ethanol. The mother liquor from the leuco product is allowed to stand for two weeks in an unstoppered flask, whereupon the oxidized product suparates. It is collected and washed with ethanol, then recrystallized from ethanol, giving blue-black crystals, m.p. 175°–177° C.

EXAMPLE 8

Leuco-1,4-Bis[2-(acetamido)ethylamino]-5,8-dihydroxyanthraquinone

A solution of 12.26 g. of N-acetylethylene diamine in 100 ml. of ethanol in the procedure of Example 3 gives 15.27 g. of dark, red-brown solid, m.p. 125° C.

EXAMPLE 9

1,4-Bis[2-(acetamido)ethylamino]-5,8-dihydroxyanthraquinone

A suspension of 11.95 g. of leuco-1,4-bis-[2-(acetamido)ethylamino]-5,8-dihydroxyanthraquinone is oxidized with 6.76 g. of chloranil during 61 hours by the method of Example 4, giving a very acidic hydrochloride salt which is converted to the free base by four washings with water. Crystallization from 110 ml. of dimethyl sulfoxide (boiling only 2 minutes and not attempting a hot filtration), then washing with dimethyl sulfoxide and with ethanol gives 7.76 g. of blue-black solid, m.p. 273°–274° C.

EXAMPLE 10

1,4-Bis[2-[N-(2-hydroxyethyl)triflouroacetamido]-ethylamino]-5.8-dihydroxyanthraquinone A suspension of 1.50 g. of 1,4-bis[2(2-hydroxyethylamino)ethylamino]-5,-dihydroxyanthraquinone in 75 ml. of ethyl triflouroacetate and 75 ml. of methanol is stirred for 10 minutes. Evaporation of the resulting solution in vacuo at 30° C. leaves a residue which is washed and macerated with methylene chloride, giving 2.11 g. of blue-black solid, m.p. 162 ° C.

EXAMPLE 11

N,N'-[5.8-Dihydroxy-1,4-anthraquinonylene-bis-(iminoethylene)]bis[N-2-hydroxyethylacetamide-2,2'-diacetate]

A mixture of 30.0 g of 1,4-dihydroxy-5,8-bis-[[2-(2-hydroxyethylamino)ethyl]amino]-anthraquinone dihydrochloride (U.S. Pat. No. 4,197,249) and 300 ml of methanol was chilled in an ice bath in a Dewar flask. The mixture was saturated with ammonia gas and stirred at 0° C. for one hour with the continuous slow addition of ammonia gas. The solid was collected and washed by slurrying with five 150 ml portions of ammonia saturated methanol, giving 22.9 g of 1,4-dihydroxy-5,8-bis[[2-(2-hydroxyethylamino)ethyl]amino]anthraquinone free base as blue-black microrods, mp 175°–178° C.

To a solution of 3.0 g of the above free base in 30 ml of glacial acetic acid, obtained by warming at 95° C., the cooling, was added 30 ml of acetic anhydride. The solution was allowed to stand 4 days then poured into 350 ml of a mixture of ice and water, agitated vigorously and then allowed to stand at 5° C. for 48 hours. The reaction mixture was extracted with three 100 ml portions of chloroform and each extract washed with three 100 ml portions of water. The chloroform extracts were combined, dried and evaporated in vacuo. The residue was dissolved in 40 ml of hot benzene and allowed to stand for 16 hours at room temperature. Seed crystals were produced by crystallizing a portion of the heavy immiscible oil in ether. These crystals were used to seed the main reaction mixture in benzene. After standing 24 hours the solid was collected, washed with benzene, then ether and dried, giving 2.88 g of the desired product as a blue-black solid, mp 140°–142° C.

EXAMPLE 12

N,N'-(5,8-Dihydroxy-1,4-anthraquinonylene)bis[2,2,2-trifluoro-N-[2-(2;2,2-trifluoro-N-2-hydroxyethyl-acetamido)ethyl]acetamide]tetrakis(trifluoroacetate) (tetraester)

A suspension of 1.37 g of 1,4-dihydroxy-5,8-bis-[[2-(hydroxyethylamino)ethyl]amino]anthraquinone free base in 10 ml of trifluoroacetic anhydride was stirred for 30 minutes, then the reaction vessel was stoppered, allowed to stand 21 hours and then evaporated to dryness in vacuo at <30° C. The residue was reevaporated three times with 20 ml portions of acetone and the final residue dried in vacuo at 40° C. for 20 hours, giving 3.23 g of the desired product as a red-orange solid mp 70° C.

EXAMPLE 13

2,2'-[(9–10-Dihydro-5,8-dihydroxy-9.0-dioxo-1,4-anthracenediyl)bis(imino-2,1-ethanediylimino)]-bis-2-oxoacetic acid]dimethyl ester A 26.0 g amount of 1,4-bis[(2-aminoethyl)amino]-5,8-dihydroxyanthraquinone dihydrochloride was converted to the free base form by treating in aqueous solution with ammonium hydroxide.

A suspension of 2.5 g of the above free base in 35 ml of dry N,N-dimethylformamide containing 5.90 g of dimethyl oxalate was stirred for 24 hours. The resulting solid was collected and washed as follows, saving each washing separately: (A) 20 ml of N,N-dimethylformamide; (B) 15 ml of chloroform:methanol (3:1); (C,D,E) three times with 50 ml portions of chloroform:methanol (3:1). Examination of the washes by TLC on silica gel with tetrahydrofuran:water:acetic acid (4:2:1) showed that B and C contained the desired product. These were evaporated, the solids combined ' and washed with acetone, giving 1.0 g of the desired product as a blue-black solid, mp 190°–193° C.

EXAMPLE 14

[(9,10-Dihydro-5,8-dihydroxy-9,10-dioxo-1.4anthracenediyl)bis(imino-2,1-ethanediyl)]-bis-[carbamic acid]diethyl ester To a stirred suspension of 2.5 g of 1,4-bis(2-aminoethyl)amino]-5,8-dihydroxyanthraquinone free base in 25 ml of pyridine at 0° C. was added dropwise 1.43 ml of ethyl chloroformate. This mixture was stirred 2 hours at room temperature, then poured into a stirred mixture of ice and water. The resulting solid was collected, washed with water and dried, giving 2.75 g of the desired product as a dark blue solid, mp 124°–129° C.

EXAMPLE 15

N,N'-[9,10-Dihydro-5.8-dihydroxy-9,10-dioxo-1,4-anthracenediyl)bisimino-2,1-ethanediyl]bis-[2-oxopropanamide]

A 2.5 g amount of 1,4-bis[(2-aminoethyl)amino]-5,8-dihydroxyanthraquinone free base was added to 5.81 g of ethyl pyruvate in 35 ml of N,N-dimethylformamide. The mixture was stirred for 2.5 hours and the solid was collected and washed with ether, giving 2.28 g of the desired product as a blue-black solid, mp 250° C.

EXAMPLE 16

N,N'-[(9,10-Dihydro-5,8-dihydroxy-9,10-dioxo-1,4,-anthracenediyl)bis(imino-2,1-ethanediyl)]bis-formamide To a stirred suspension of 3.56 g of 1,4-bis[(2-aminoethyl)amino]-5,8-dihydroxyanthraquinone free base in 50 ml of 90% formic acid was added 7.0 ml of aceticformic anhydride [J. Muramatsu, et al., Bul. Soc. Chem. Japan, 38, 244 (1945)]. This solution was stirred for one hour, then poured into 350 ml of water with stirring and made basic by the addition of ammonium hydroxide. The resulting solid was collected, air dried, then dried in vacuo at 75° C. for 16 hours, giving 4.04 g of the desired product as a blue-black solid.

We claim:

1. A compound selected from the group consisting of those of the formula:

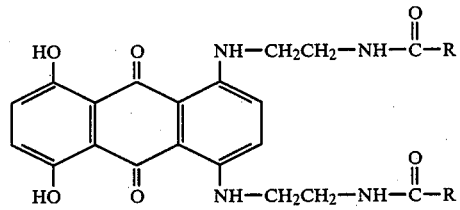

wherein R is hydrogen, alkyl ($C_1$–$C_3$), trifluoromethyl, acetyl, ethoxy or carbomethoxy; the leuco bases and tautomers thereof; and the pharmacologically acceptable acid-addition salts thereof.

2. The compound according to claim 1 wherein R is hydrogen; N,N'-[10-dihydro-5,8-dihydroxy-9, 10-dioxo-1,4-anthracenediyl)bis(imino-2, 1-ethanediyl)]bis-formamide.

3. The compound according to claim 1 wherein R is methyl; N,N'-[(9,10-dihydro-5,8-dihydroxy-9, 10-dioxo- 1,4-anthracenediyl)bis(imino-2, 1-ethanediyl)]bis-acetamide.

4. The compound according to claim 1 wherein R is trifluoromethyl; N,N'-[(9,10-dihydro-5,8-dihydroxy-9,10-dioxo-1,4-anthracenediyl)bis-(imino-2,1-ethanediyl)]bis-trifluoroacetamide.

5. The compound according to claim 1 wherein R is acetyl; N,N'-[(9,10-dihydro-5,8-dihydroxy-9,10-dioxo-1,4-anthracenediyl)bis(imino-2,1-ethanediyl)]bis-(2-oxopropanamide).

6. The compound according to claim 1 wherein R is ethoxy;[(9,10-dihydro-5,8-dihydroxy-9,10-dioxo-1,4-anthracenediyl)bis(imino-2,1-ethanediyl)]-bis-(carbamic acid)diethyl ester.

7. The compound according to claim 1 wherein R is carbomethoxy; 2,2'-[(9,10-dihydro-5,8-dihydroxy-9,10-dioxo-1,4-anthracenediyl)bis(imino-2,1-ethanediylimino)]bis(2-oxoacetic acid)dimethyl ester.

8. A compound selected from the group consisting of 1,4-bis[2-[N-(2-hydroxyethyl)trifluoroacetamido]ethylamino]-5,8-dihydroxyanthraquinone, the leuco base and tautomer thereof, and the pharmacologically acceptable acid-addition salts thereof.

9. A compound selected from the group consisting of N,N'-[5,8-dihydroxy-1,4-anthraquinonylene-bis(iminoethylene)]bis[N-2-hydroxyethylacetamide-2,2'-diacetate],the leuco base and tautomer thereof, and the pharmacologically acceptable acid-addition salts thereof.

10. A compound selected from the group consisting of N,N'-(5,8-dihydroxy-1,4-anthraquinonylene)-bis[2,2,2-trifluoro-N-[2-(2,2,2-trifluoro-N-2-hydroxyethylacetamido)ethyl]acetamide]tetrakis(trifluoroacetate)(tetraester), the leuco base and the tautomer thereof, and the pharmacologically acceptable acid-addition salts thereof.

* * * * *